United States Patent [19]

Makino et al.

[11] Patent Number: 5,130,258

[45] Date of Patent: Jul. 14, 1992

[54] METHOD OF QUANTITATIVELY ANALYZING ANALYTE CONTAINED IN WHOLE BLOOD SAMPLE

[75] Inventors: Yoshihiko Makino; Masashi Ogawa, both of Saitama, Japan

[73] Assignee: Fuji Photo Film Co., Ltd., Kanagawa, Japan

[21] Appl. No.: 643,831

[22] Filed: Jan. 18, 1991

[30] Foreign Application Priority Data

Jan. 19, 1990 [JP] Japan ..................... 2-10426

[51] Int. Cl.$^5$ ................. G01N 21/47; G01N 21/77; G01N 33/52

[52] U.S. Cl. ................. 436/169; 436/178; 436/805; 436/808; 436/824; 422/55; 422/56; 435/4; 435/219; 435/805; 435/810

[58] Field of Search ................. 422/55–58, 422/61; 436/63, 169–171, 175, 178, 805, 807, 808, 810, 823, 824; 435/4, 219, 805, 810

[56] References Cited

U.S. PATENT DOCUMENTS

| | | | |
|---|---|---|---|
| 4,292,272 | 9/1981 | Kitajima | 422/57 |
| 4,424,191 | 1/1984 | Jakubowicz | 422/65 |
| 4,889,797 | 12/1989 | Amano | 435/4 |

*Primary Examiner*—James C. Housel
*Assistant Examiner*—David Redding

*Attorney, Agent, or Firm*—McAulay Fisher Nissen Goldberg & Kiel

[57] ABSTRACT

A method of quantitatively analyzing an analyte contained in a whole blood sample, wherein a dry multi-layered analysis element is used. The method provides particular merits when the used multi-layered analysis element has no light-shielding layer which is interposed, in the conventional analysis element, between a coloring reagent layer and a blood cell separating layer, so that red coloring matters of blood cells are detected from the support side during the step of measuring the optical density of the reflected light. After the optical density due to coloring matters of blood cells trapped by the blood cell separating layer has reached a constant level or background density, the changing rate in optical density is measured and then the measured changing rate is converted to the corresponding content or activity of the analyte through a colorimetric operation, or the total change in optical density is measured and then the substantially constant background density is subtracted therefrom to know the change in optical density caused by a coloring dye or like material formed in the coloring reagent layer in the presence of the analyte, followed by a similar conversion operation performed on the basis of the principle of colorimetry, to determine the content or activity of the analyte.

18 Claims, 3 Drawing Sheets

METHOD OF QUANTITATIVELY ANALYZING ANALYTE CONTAINED IN WHOLE BLOOD SAMPLE

BACKGROUND OF THE INVENTION

1. Field of the Invention

The present invention relates to a method of quantitatively analyzing the concentration or activity of an analyte contained in a whole blood sample by using a dry analysis element.

2. Prior Art

It is important to determine the content or activity of an analyte in a living body fluid, particularly in blood, for example, for the diagnosis of diseases or for monitoring the course of remedy. For such purpose, dry chemical analysis elements (or strips) have been increasingly used in recent years, since they are economical and operable with ease to give test results rapidly. The dry chemical analysis is a method wherein a test strip or multi-layered analysis element is used in the dry state different from the conventional chemical analysis conducted in a wet system. Dry analysis elements are disclosed, for example, in Japanese Patent Publication No. 21677/1978 (corresponding to U.S. Pat. No. 3,992,158), Unexamined Japanese Patent Publication No. 164356/1980 (corresponding to U.S. Pat. No. 4,292,272) and Unexamined Japanese Patent Publication No. 222769/1985 (corresponding to EP 0 162 302A). The dry multi-layered analysis element comprises, for example, a transparent support, a reagent layer and a spreading layer. The transparent support is made of, for example, a thin light-permeable and water-impermeable organic polymer sheet. The reagent layer is coated over the transparent support and contains a reagent composition which reacts with the analyte in a liquid sample taken from a living body to give some change in signal, for example, change in color density due to coloring by a formed dye, the color change being in proportion to the quantity of analyte contained in the sample. The spreading layer spreads the liquid sample spotted thereon uniformly so that a spread area is in proportion to the volume of the spotted liquid sample.

When a dry multi-layered analysis element is used for the quantitative analysis, a proper volume of a liquid sample is spotted on the surface of the spreading layer by dropping or otherwise applying the liquid sample. The liquid sample is uniformly spread within the spreading layer to be passed to the reagent composition layer where the analyte contained in the sample reacts with the reagent composition to exhibit a change in some signal. The analysis element is held at a constant temperature for a sufficient time period for completing the reaction (incubation), and then the change in some signal is detected. When the signal is a color change due to formation of some dye, the reagent composition layer is irradiated with a light from the transparent support side and the optical density of the reflected light is measured at a certain wavelength. The content (concentration or activity) of the analyte may be colorimetrically determined by comparing the thus detected signal change with a calibration curve (or table) which is preliminarily drawn by plotting the interrelation between the signal change and the content of analyte in the liquid sample. The signal change may be the absolute value of a parameter after the lapse of a predetermined time from the time at which the liquid sample is spotted, or may be the changing rate within a unit time.

However, when a whole blood sample is to be analyzed by the use of most of the conventionally proposed or commonly used dry analysis elements, it becomes necessary to remove blood cells from the whole blood sample to separate blood serum or plasma, generally by means of centrifugal separation, since whole blood cannot be used directly as a liquid sample in some dry analysis elements. For this reason, irrespective of the merits of the analysis in which dry analysis elements are used, i.e. easy handling, rapidity and economical saving attainable by the use of the dry analysis element, practical utility thereof is reduced seriously since it requires considerable labours and time with the need of using an expensive equipment to remove blood cells from the whole blood sample.

In quantitative analysis of an analyte contained in a whole blood sample by using a dry analysis element, it is required (1) to remove blood cell components, particularly red blood cells, from the sample by any means or reaction, and in addition (2) to prevent the red metters (hemoglobin) of the separated blood cells from hindering the operation of measuring the optical density. Japanese Patent Publication No. 21677/1978 (corresponding to U.S. Pat. No. 3,992,158) discloses that a filtering layer is disposed within an analysis element for separating and removing blood cells contained in whole blood. However, it requires longer time to remove blood cells from whole blood to separate blood serum or plasma by the filtering layer. Furthermore, there is a fear that a portion of the analyte to be analyzed might be lost during the filtering operation or hemolysis of red blood cells might occur to result in inaccurate analysis.

On the other hand, Unexamined Japanese Patent Publication No. 138756/1987 (correponding to EP 0 226 465A) proposes a dry analysis element conveniently used for the quantitative analysis of an analyte in a whole blood sample, in which removal of blood cells in the whole blood sample is accelerated so that the analyte in the separated plasma is rapidly spread into the reagent composition layer. However, the analysis element of this prior proposal has a disadvantage that the results of analysis are affected by the hematocrit values of individual blood samples to give different test results even when the contents of analyte in respective samples are same. Accordingly, it is difficult to perform accurate analysis when such an analysis element is used. Unexamined Japanese Patent publication No. 54354/1989 (corresponding to EP 0 302 287A) proposes the provision of a light-shielding layer containing a white pigment to shield the light irradiated for the purpose of determination so as to eliminate the influence of red matters contained in red blood cells. It is estimated that the provision of such a light-shielding layer is effective for excluding the influence by the red matters contained in red blood cells to improve the accuracy of the determination operation. However, the particle size and dispersion of the pigment particles must be precisely controlled in order to adjust the light-shielding rate, leading to complication of the production steps and increase in production cost. In addition, there is found a case where separation of blood cell components cannot be performed sufficiently or sufficient amount of separated plasma is not fed into the reagent composition layer.

OBJECTS AND SUMMARY OF THE INVENTION

An object of this invention is to provide a method of quantitatively analyzing an analyte contained in a whole blood sample while using a dry multi-layered analysis element in which blood cells are rapidly removed from the whole blood sample.

Another object of this invention is to provide a method of quantitatively analyzing an analyte contained in a whole blood sample while using a dry multi-layered analysis element in which coloring matters contained in the thus separated blood cells do not hinder the subsequent processing steps.

A further object of this invention is to provide such a method for performing rapid and precise quantitative analysis of an analyte without being affected by the hematocrit value of the used whole blood sample.

With the aforementioned objects in view, the present invention provides an improvement in the method of quantitatively analyzing an analyte in a whole blood sample by using a multi-layered analysis element including at least a coloring reagent layer in which said analyte reacts with a reagent composition to exhibit an optically detectable color change or color generation and a blood cell separating layer for separating the blood cells in the whole blood to feed blood plasma to said reagent layer, said improved method comprising the steps of:

(1) spotting a whole blood sample onto said blood cell separating layer;

(2) allowing to stand said multi-layered analysis element until the optical density of the reflected light due to the coloring matters contained in the blood cell detected from the coloring reagent layer side reaches a substantially constant level;

(3) measuring the rate of change or generation in optical density within a unit time in said coloring reagent layer from the coloring reagent layer side; and (4) colorimetrically determining the quantity of said analyte depending on the rate of change in optical density measured by the preceding step (3).

The present invention also provides an improvement in the method of quantitatively analyzing an analyte in a whole blood sample by using a multi-layered analysis element including at least a coloring reagent layer in which said analyte reacts with a reagent composition to exhibit an optically detectable color change or color geneation and a blood cell separating layer for separating the blood cells in the whole blood to feed blood plasma to said reagent layer, said improved method comprising the steps of:

(1) spotting a whole blood sample onto said blood cell separating layer;

(2) allowing to stand said multi-layered analysis element until the optical density of the reflected light due to the coloring matters contained in the blood cells detected from the coloring reagent layer side reaches a substantially constant level;

(3) measuring the total optical density of the reflected light from the coloring reagent layer side, said total optical density being the sum of the optical density of the reflected light due to the color change or color generation of said analyte and the optical density of the reflected light due to the coloring matters contained in the blood cells;

(4) determining the difference in optical density between said total optical density measured in said step (3) and the optical density measured in said step (2); and (5) colorimetrically determining the quantity of said analyte depending on the difference in optical density determined by the preceding step (4).

DESCRIPTION OF PREFERRED EMBODIMENTS

Figure 1:
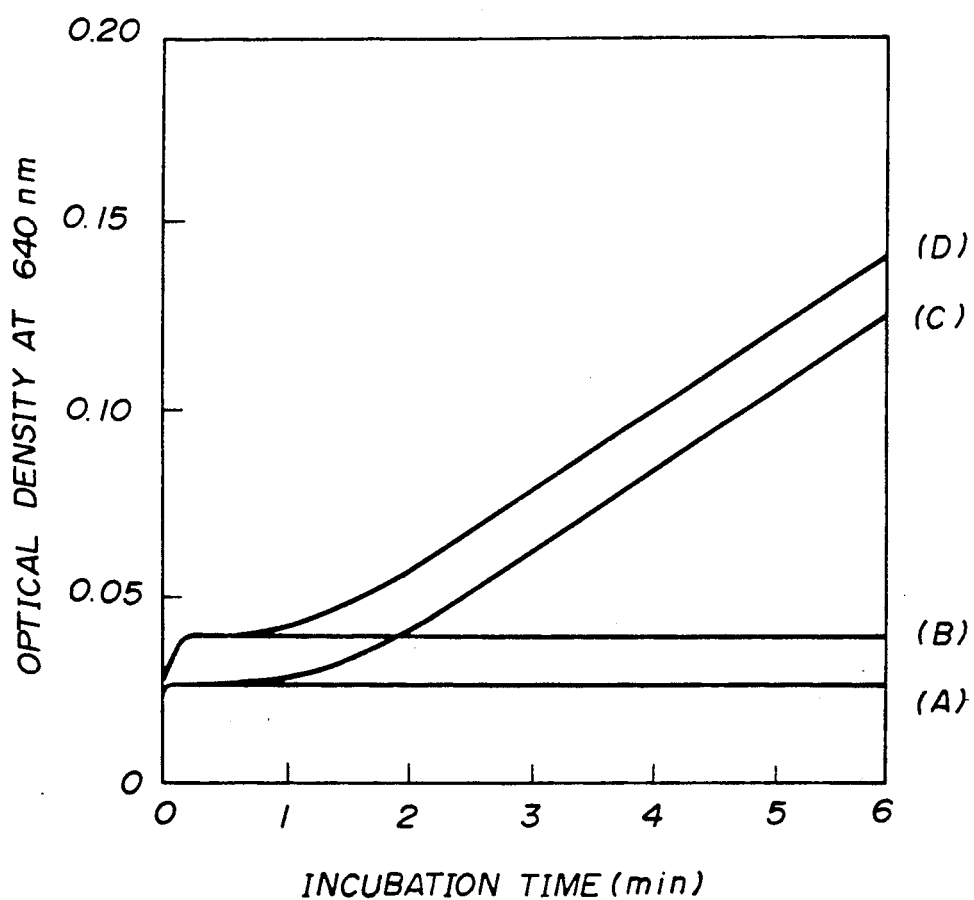
FIG. 1 is a graph drawn by plotting the optical densities of reflected lights measured from the light irradiating side (through the transparent support) at a wavelength of 640 nm, each of the optical densities being measured, according to one embodiment of the invention, after spotting liquid samples and allowing respective multi-layered analysis elements to stand at 37° C. for a certain time in an incubator.

Details of the method of this invention will be described below.

In the method of the invention, a multi-layered analysis element comprising at least a coloring reagent layer and a blood cell separating layer is used. It is preferable that blood cell components in the whole blood sample have been completely removed in the used multi-layered analysis element before the change (or generation) in optical density caused by the reaction of the analyte in the reagent composition layer is detected. It is also preferable that the optical density of the coloring matters contained in the separated blood cells reaches a constant level to be detected by proper optical means from the transparent support layer side. The coloring reagent composition layer is connected to the blood cell separating layer to form an integral lamination construction preferably by using an adhesive partially placed not to hinder uniform passage of the liquid ingredient from the blood cell separating layer to the coloring reagent composition layer.

The dry multi-layered analysis element used in the method of this invention is essentially consisting of an underlying composite in which the analyte contained in the whole blood sample reacts with the reagent composition to exhibit a signal change in proportion to the content of the analyte in the sample, and a layer (blood cell separating layer) for removing blood cells from the whole blood sample to feed plasma into the underlying composite.

The underlying composite may be composed of a known dry multi-layered analysis element which has been previously used as an analysis element for the blood serum or plasma. In detail, the underlying composite may comprises a transparent support, a coloring reagent layer laminated on the support and a spreading layer laminated on the coloring reagent layer. A detection layer or a water-absorbing layer may be interposed between the support and the coloring reagent layer. However, the support is not essential when the shape and function of the finished analysis element can be retained by any of the layers other than the support layer. When it is desired to measure the optical density of the colored analyte directly without passing the light through the support, the support may be peeled off the coloring reagent layer (or from the detection or water-absorbing layer).

Transparent Support

The transparent support is preferably water-impermeable. Preferred materials for the transparent support include, for example, polyethylene terephthalate, polycarbonate of bisphenol-A, and cellulose esters such as cellulose triacetate and cellulose acetate butyrate. It is preferred that the surface of the support is hydrophilized, for example by subjecting the same to physicochemically activating treatment (e.g. corona discharge treatment) or by applying a hydrophilic coating, so as to ensure firm bonding with the coloring reagent, water-absorbing or detection layer which generally contains a hydrophilic polymer binder.

Coloring Reagent Layer

The coloring reagent layer contains a reagent composition which reacts with the analyte to produce a dye or similar optically detectable material. Examples of preferred reagent composition include compositions which produce dyes by the oxidation of leuco dyes, such as triarylimidazole leuco dyes disclosed in U.S. Pat. No. 4,089,747 and diarylimidazole leuco dyes disclosed in Unexamined Japanese Patent Publication No. 19332/1984 (corresponding to EP 0 122 641A); diazonium salts; pH indicator dyes, for example, bromcresol green, or compositions each containing a dye forming compound (a chromogen compound) which couples with a coupler upon oxidation to form a dye, for example combinations of 4-aminoantipyrine and phenols or naphthols; and compositions each containing a compound which forms a dye in the presence of a reducing coenzyme and an electron transmitting agent. On the other hand, when an enzymatic activity of the analyte is analyzed, the reagent composition may contain an autocoloring substrate which releases a coloring material, such as p-nitrophenol and p-nitrophenyl phosphate. An appropriate reagent composition may be selectively used depending on the analyte contained in the whole blood sample.

All components of the reagent composition may be contained in a single layer, or they may be separatedly contained in plural layers. For example, a solution of a hydrophilic polymer containing a portion or all of the reagent composition may be applied on the hydrophilized surface of the support, followed by drying, to form a substantially uniform layer composed of the hydrophilic polymer binder in which a portion or all of the reagent composition is contained. Examples of preferred hydrophilic polymer include gelatin and derivatives thereof, such as phthalated gelatin; derivatives of cellulose such as hydroxypropyl cellulose; agarose; acrylamide polymers; methacrylamide polymers; and copolymers of acrylamides or methacrylamides with various vinyl monomers. Alternatively, a porous layer containing no reagent composition may be laminated on a uniform layer containing a hydrophilic polymer binder in which a portion or all of the reagent composition is contained, for example, by a process as disclosed in Unexamined Japanese Patent publication No. 164356/1980 (corresponding to U.S. Pat. No. 4,292,272), and then a solution or dispersion containing the remaining portion or all of the reagent composition is coated over the porous layer to impregnate the reagent composition into the porous layer.

The porous layer may be bound to or laminated on the reagent layer through an adhesive layer. The adhesive layer is preferably composed of a hydrophilic polymer, such as gelatin, derivatives of gelatin or polyacrylamides, so that it adheres to the porous layer upon wetting with water. A portion of the reagent composition may be contained in the adhesive layer.

It is preferred that the porous layer is a layer having the metering function, since it serves as a spreading layer in the underlying composite of the analysis element. The metering function means the function of uniformly spreading the liquid sample fed by spotting onto the surface of the spreading layer so that a constant volume of liquid sample is dispersed uniformly within a unit area not to leave any portion in which the liquid sample is present in a concentrated or diluted condition. In the multi-layered analysis element used in the method of the invention, the term "metering function" means that the plasma passing through the blood cell separating layer is spread substantially uniformly to cover a certain area within which plasma is distributed at a substantially constant ratio.

Either of a non-fibrous layer or a fibrous layer may be used as the porous layer. Preferred examples of the non-fibrous porous layer include layers made of blush polymers selected, for example, from cellulose esters, such as cellulose acetate, cellulose acetate butyrate and cellulose nitrate, as disclosed in Japanese Patent Publication No. 21677/1978 (corresponding to U.S. Pat. No. 3,992,158) and U.S. Pat. No. 1,421,341. Other preferable examples are micro-porous layers made of, for example, polyamides such as 6-nylon and 6,6-nylon, polyethylene or polypropylene, and micro-porous layers made of polysulfone as disclosed in Unexamined Japanese Patent Publication No. 27006/1987 (Chemical Abstracts 106, 140291K).

Examples of the material for forming the fibrous porous layer include filler paper, non-woven cloths, woven cloths such as plain woven cloth, knitted cloths such as tricot knitted cloth, and glass fiber filter paper or mat. Woven cloths and knitted cloths are preferred. Woven cloths or other materials may be subjected to physicochemical treatment (e.g. glow discharge treatment) as disclosed in Unexamined Japanese Patent Publication No. 66359/1982 (corresponding to U.S. Pat. No. 4,783,315).

The porous layer may contain a hydrophilic polymer or a surface active agent, as disclosed in Unexamined Japanese Patent Nos. 222770/1985 (corresponding to EP 0 162 301A), 219397/1988 (corresponding to EP 0 254 202A), 112999/1988 (corresponding to U.S. Pat. No. 4,889,797) and 182562/1988 (corresponding to DE 3717913A).

In the conventional multi-layered analysis elements, fine light-reflecting and light-shielding particles, such as titanium dioxide or barium sulfate, are dispersed in the porous layer, or a hydrophilic polymer binder layer made of gelatin or like material, in which fine light-reflecting and light-shielding particles are dispersed, is provided. However, such particles need not be dispersed in the porous layer of the multi-layered analysis element used in the method of the invention. The underlying composite of the multi-layered analysis element used in the method of the invention may also be used for an analysis element on which blood serum or plasma is spotted. By selecting a proper reagent composition which is contained in the underlying composite, an analysis element for the quantitative analysis of AST (aspartate aminotransferase), ALT (alanine aminotransferase), LDH (lactic dehydrogenase), creatine kinase, amylase, cholesterol, bilirubin or uric acid maybe prepared.

Blood Cell Separating Layer

An effective blood cell separating layer may be prepared by integrating or binding a fibrous porous layer with a non-fibrous porous layer through a partial bonding technique in which the halftone printing process, such as the gravure printing or screen printing process, is utilized.

A typical spot bonding technique utilizing the gravure printing process comprises the steps of heating a hot-melt type adhesive at a high temperature to melt the adhesive, applying the molten adhesive over a gravure roller, transferring the molten adhesive from the gravure roller onto the surface of either one of the fibrous or non-fibrous porous layers overlaying the fibrous porous layer on the non-fibrous porous layer in the condition such that the dotted adhesive pattern is sandwiched between both layers and then passing the superposing layers through a laminate roller pair. An example of this process is described in Unexamined Japanese Patent Publication No. 138756/1987 (corresponding to EP 0 226 465A). The thus prepared blood cell separating layer is composed of the fibrous porous layer which is integrally bound to the non-fibrous porous layer by the adhesive applied to form a dotted pattern not to hinder passage of liquid ingredients. The blood cell separating layer is arranged with the fibrous porous layer facing upside, in other words, the fibrous porous layer is arranged closer to the surface on which the whole blood sample is spotted.

Since the fibrous porous layer of the blood cell separating layer serves also as a spreading layer when the whole blood sample is spotted or fed thereon, it is preferred that this layer exhibits the liquid metering function.

Similar materials used for forming the fibrous reagent composition layer may be used as the materials for forming the fibrous porous layer of the blood cell separating layer.

When it is desired to add a hydrophilic polymer or a surface active agent to the fibrous porous layer in order to control the extention or spread area within which the spotted liquid sample is spread or to control the spreading rate, the hydrophilic polymer and/or the surface active agent should be selected from those which do not cause hemolysis in the layer. A hydrophilic polymer and/or an inorganic salt which accelerate separation of blood cells may also be contained in the fibrous porous layer.

Similar materials used for forming the non-fibrous reagent composition layer may be used as the materials for forming the non-fibrous porous layer of the blood cell separating layer.

When the non-fibrous porous layer is made of a membrane filter composed of a so-called blush polymer prepared through the phase separation process, the narrowest portion along the height direction of the liquid passage is positioned across the free surface (i.e. glossy surface) which is formed during the step of preparing the membrane. In other words, assuming now that the cross section of the liquid passage is proximate to a circle, the diameter of the circumference of the liquid passage is the smallest at the vicinity of the free surface. Such a blush polymer is preferably used as the material for the non-fibrous porous layer of the blood cell separating layer. When a blush polymer membrane is used to form the blood cell separating layer, the upper fibrous layer is bound to the lower non-fibrous layer with the glossy surface of the blush polymer is arranged at the side remoter from the upper fibrous layer of the blood cell separating layer. With this construction, the liquid passage through the non-fibrous layer is converged as it extends remoter from the fibrous porous layer.

It is preferred that the non-fibrous porous material used to form the underlying layer in the blood cell separating layer has an effective pore size ranging from about 0.8 $\mu$m to about 30 $\mu$m. The effective porous size, as used herein, is determined by a bubble point method which is generally similar to the method stipulated in ASTM F-316-70. If the effective pore size of the non-fibrous porous layer of the blood cell separating layer is excessively large, satisfactory separation and removal of blood cells from the whole blood sample cannot be achieved so that a portion of blood cells passes to the underlying composite of the multi-layered analysis element to hinder the coloring reaction of the analyte with the reagent composition, leading to failure of accurate quantitative analysis. On the contrary, if the effective pore size of the non-fibrous porous layer is too small, heavy shearing stress is applied on the blood cells passing through the non-fibrous porous layer to cause hemolysis of the red blood cells, so that ingredients contained in blood cells are released to change the concentration or activity of the analyte contained in the whole blood sample, leading to failure of accurate quantitative analysis.

Accordingly, the pore size of the non-fibrous porous layer of the blood cell separating layer should be selected such that the moving speed of the blood cells, particularly red blood cells, through the non-fibrous porous layer is differentiated from the moving speed of the plasma while the resistance or arresting force applied on the blood cells is low enough to prevent hemolysis of red blood cells.

Lamination of the Underlying composite with the Blood Cell Separating Layer

The blood cell separating layer is laminated on the underlying composite preferably by partial adhesion (partial bonding) utilizing the halftone printing process (e.g. the gravure or screen printing process) to prepare an integral multi-layered analysis element. When a hot-melt type adhesive is used and the gravure printing process is employed, the adhesive is heated at a high temperature to melt the same and the molten adhesive is transferred onto one surface of either one of the underlying composite or the blood cell separating layer. The porous layer of the underlying composite laminated with the non-fibrous porous layer of the blood cell separating layer by partial-bonding.

The multi-layered analysis element used in the method of this invention comprises the water-impermeable and light-permeable support (i.e. the transparent support), the underlying composite laminated on the support, and including the coloring reagent layer in which the analyte contained in the whole blood sample reacts with the reagent composition to cause a certain detectable generation or change in color or optical density, and the blood cell separating layer for separating and removing the blood cells from the whole blood sample to pass the plasma to the coloring reagent layer, the blood cell separating layer being laminated on the underlying composite, whereby an integral laminated structure is formed. It should be noted here that the analysis element used in the method of this invention does not have a light-shielding or light-reflecting layer which is provided in the prior art multi-layered analysis element for preventing detection of the coloring materials of the blood cells separated and removed from the whole blood sample. Exclusion of such a light-shielding or light-reflecting layer is one of the important features of the analysis element used in the method of this invention.

Processing Steps Taking Place During the Quantitative Analysis

When using the dry multi-layered analysis element described in detail hereinbefore, an analyte contained in the whole blood sample is quantitatively analyzed as follows.

A constant volume (e.g. 20 μl) of a whole blood sample taken, for example, from a human being is spotted on the top surface of the fibrous porous layer which is the uppermost layer remotest from the transparent support of the integral analysis element. The spotted whole blood sample is spread substantially uniformly on the fibrous porous layer to cover a certain area. As the whole blood sample moves downwards across the blood cell separating layer where the blood cells are separated from the plasma by the cooperative functions of the fibrous porous layer and the non-fibrous porous layer, so that all of the blood cells are blocked to prevent arrival thereof to the lower surface of the non-fibrous porous layer while the plasma is allowed to pass through the blood cell separating layer into the porous underlying composite of the analysis element. The separated plasma fed to the porous layer of the underlying composite is substantially uniformly spread to be distributed within an area which extends in proportion to the volume of the plasma fed to the underlying composite.

It is surprising that the blood cells contained in the spotted whole blood sample are separated and trapped substantially completely not to move onto the under surface of the non-fibrous porous layer of the blood cell separating layer. The mechanism of such complete separation of blood cells by the blood cell separating layer has not been theoretically clarified. However, it is at least estimated that the mechanism does not depend on a so-called physical filtration in which the blood cells are separated by blocking passage of particles having large size. If it is intended to separate the blood cells from the whole blood sample by means of physical filtration, serious shearing load is applied on each red blood cell to cause hemolysis. However, as will be demonstrated in Examples given hereinafter, hemolysis of red blood cells is not observed in the multi-layered analysis element used in the method of this invention. Separation and removal of blood cells by the blood cell separating layer is completed rapidly after the whole blood sample is spotted on the fibrous porous layer of the blood cell separating layer. Separation and removal of blood cells is completed within 30 seconds at the latest. Different from the analysis elements proposed and used by the conventional technology, the multi-layered analysis element, described in detail hereinbefore and used in the method of the invention, does not exhibit the light-shielding function for preventing detection of coloring matters present in the layers upside of the coloring reagent layer. Accordingly, the coloring matters (particularly red dyes, i.e. hemoglobin, of the red blood cells) of the blood cells are optically detected from the transparent support side immediately after the whole blood sample is spotted. The optical density of the reflected light, due to the coloring matters in the blood cells, is saturated at the time when the blood cells have been completely separated to take an constant absolute value which is determined by the hematocrit value or other parameters of the individual whole blood sample. After the complete removal of blood cells, the optical density due to the presence of the separated blood cells is not changed.

After the completion of removal of blood cells, the plasma is spread substantially uniformly as it passes through the porous layer of the underlying composite of the analysis element, and then the analyte contained in the plasma reacts with the coloring reagent composition contained in the underlying composite of the analysis element to exhibit a change in optically detectable signal independently of the optical density due to the coloring matters in the separated blood cells.

In the quantitative analysis of an analyte contained in the whole blood sample while the aforementioned multi-layered analysis element, the optical density of the reflected light due to the dye formed or the change of color by the reaction between the analyte and the coloring reagent composition is detected after the optical density of the reflected light due to the coloring materials of the separated blood cells has been saturated.

When a multi-layered analysis element having no transparent support is used or when the transparent support is peeled off before the measurement of optical density, instead of measuring the optical density through the transparent support, the under surface of the coloring reagent layer, which is opposite to the top surface where the whole blood sample has been spotted, is exposed to a light and the optical density of the reflected light is measured.

Using the thus measured optical density as a parameter for the colorimetric determination, the content or quantity of the analyte contained in the spotted whole blood sample can be determined by referring to the interrelation between the parameter and content or quantity of the analyte (the interrelation being plotted to draw a calibration curve in most cases). The parameter may be the change in optical density of the reflected light per a unit time after the lapse of a predetermined time period from the time when the whole blood sample is spotted, or may be the absolute optical density of the reflected light measured after the lapse of a predetermined time period from the time when the whole blood sample is spotted.

When the change in optical density of the reflected light per a unit time is used as the parameter, the measured value need not be corrected. After the time when the background optical density due to the coloring matters (mainly due to hemoglobin) contained in the separated blood cells has been saturated, the changing rate in optical density of the reflected light is not affected by the background optical density.

On the contrary, when the absolute value of the optical density of the reflected light measured after the lapse of a predetermined time is used as the parameter, the total optical density is the sum of the optical density due to the analyte and the optical density due to the coloring matters contained in the separated blood cells (i.e. the background optical density). Accordingly, the real parameter value should be obtained by subtracting the background optical density, which has been saturated to take a constant value after the lapse of the predetermined time period, from the total optical density.

The volume of the whole blood sample required for the practice of the method of this invention ranges generally from about 5 μl to about 30 μl, preferably from about 8 μl to about 15 μl. In the method of the quantitative analysis of an analyte, according to the invention, after the optical density of the reflected light, due to the coloring matters in the blood cells separated from the whole blood sample, detected from the support side has reached to a substantially constant level (about 30 seconds at the latest, normally about 20 seconds, after the time of spotting the sample), the optical density or the change in optical density per unit time of the reflected light in the coloring reagent layer is measured from the support side within a time range of from about 1 minute to about 10 minutes under incubating at a substantially constant temperature within the range of about 20° C. to about 40° C., preferably at about 37° C., and then the content or activity of the analyte is colorimetrically determined based on the detected optical density or change in optical density. The method of the invention can be applied for the quantitative analysis of an analyte easily with high accuracy while using any of the systems employed for the chemical analysis and disclosed, for example, in Unexamined Japanese Patent Publication Nos. 125543/1985, 220862/1985, 294367/1986 and 161867/1983 (corresponding to U.S. Pat. No. 4,424,191).

As will be understood from the foregoing, the present invention provides a method for the quantitative analysis in which an analyte contained in a whole blood sample can be quantitatively analyzed with high accuracy within a very short operation time of in the order of few minutes (within a time of from about 2 to 10 minutes) without being affected by the hematocrit value of the used whole blood sample, while using a multi-layered analysis element in which no light-shielding or light-reflecting layer is provided. In addition, by properly selecting the reagent composition contained in the underlying composite of the multi-layered analysis element of the invention, a variety of analytes contained in whole blood samples taken from different sources may be quantitatively analyzed accurately by a simple operation.

EXAMPLES OF THE INVENTION

The present invention will now be described more specifically in the following description by referring to some examples thereof.

EXAMPLE 1

Multi-layered Analysis Element Used for the Quantitative Analysis of ASP (Aspartate Aminotransferase) Activity 1-1: Preparation of Underlying Composite of the Analysis Element A coloring regent composition was coated on a colorless, transparent and flat sheet of polyethylene terephthalate (PET) having a thickness of 180 μm and applied with a gelatin undercoat layer, followed by drying, to form a 15 μm thick (in the dried state) coloring reagent layer having the following coverage of respective ingredients.

| Coverage (per 1 m²) of the Coloring Reagent Composition: | |
|---|---|
| Deionized Gelatin | 20 g |
| p-Nonylphenoxypolyglycidol | 1.5 g |
| (Containing 10 Glycidol Units on Average) | |
| Peroxidase | 15,000 IU |
| FAD (Flavin Adenine Dinucleotide) | 22 mg |
| TPP (Thiamine Pyrophosphate)(Cocarboxylase) | 93 mg |
| Pyruvate oxidase | 13,00 IU |
| 2-(3,5-Dimethoxy-4-hydroxyphenyl)-4-phenetyl-5-[4-(dimethylamino)phenyl]-imidazole (Leuco Dye) | 280 mg |

An aqueous solution of the coloring reagent composition set forth above was prepared and the pH value thereof was adjusted to pH 6.5 using a dilute aqueous solution of NaOH and then the solution was coated to form a coloring reagent layer.

Then, an adhesive composition as set forth below was coated on the coloring reagent layer, followed by drying, to form a 3 μm thick (in the dried state) adhesive layer having the following coverage of respective ingredients.

| Coverage (per 1 m²) of the Adhesive: | |
|---|---|
| Deionized Gelatin | 4.0 g |
| p-Nonylphenoxypolyglycidol | 430 mg |
| (Containing 10 Glycidol Units on Average) | |
| Sodium L-Asparate | 250 mg |

The overall surface of the thus formed adhesive layer was wetted uniformly with water, and a PET broad woven cloth (having a thickness of about 150 μm and a volume porosity of 9.8 μl/m²) was placed on the adhesive layer. The broad woven cloth was laminated on the adhesive layer by the application of a light pressure, and then the laminate was dried.

An aqueous solution of an AST detecting reagent composition composed of the components as set forth below was coated over the surface of the laminate uniformly in a ratio of 100 ml/m² to form a substantially uniform coating which was dried after the coated aqueous solution of the reagent composition was impregnated into the laminate, whereby an underlying composite or laminate for a multi-layered analysis element for the quantitative analysis of AST activity was prepared.

| Composition of Aqueous Solution of AST Detecting Reagent: | |
|---|---|
| Tris(hydroxymethyl)aminomethane | 3.7 g |
| Potassium Dihydrogenphosphate ($KH_2PO_4$) | 4.4 g |
| α-Ketoglutaric Acid | 4.0 g |
| Hydroxypropylmethyl Cellulose | 8.7 g |
| (Containing 28 to 30% of methoxy groups and 7 to 12% of hydroxypropoxy groups; and having a viscosity at 20° C. of a 2% solution of 50 cps.) | |
| Octylphenoxypolyethoxyethanol | 27 g |
| (Containing 10 Oxyethylene Units on Average) | |
| Magnesium Chloride | 2.3 g |
| Oxaloacetate Decarboxylase | 200,000 IU |
| Ascorbate Oxidase | 180,000 IU |
| Water | 880 g |

Prior to coating the aqueous solution of the AST detecting reagent composition, the pH value thereof was adjusted to pH 7.5 using a dilute aqueous solution of NaOH.

1-2: Preparation of Blood Cell Separating Layer

A tricot knitted cloth (Thickness: about 250 μm) was prepared by knitting a 50 denier PET spun yarn (Knitting Gauge: 36), and the knitted cloth was impregnated with an aqueous solution having the following composition and then dried.

| | |
|---|---|
| Polyethylene Glycol (Average Molelular Weight: 50,000) | 2.0 g |
| Sodium Tetraborate | 2.0 g |
| Water | 96 g |

The tricot knitted cloth impregnated with the composition set forth above was then heated to 80° C., and a hot-melt type adhesive was heated to 130° C. to be melted. The molten adhesive was applied on the heated tricot knitted cloth by the gravure printing process to form a dotted pattern of the adhesive. In detail, the molten adhesive was transferred from a gravure roller formed with a dotted pattern composed of multiple circular data each having a diameter of 0.3 mm, the center-to-center spacing between adjacent dots being 0.6 mm. About 20% of the peripheral area of the gravure roller was shared by the dots. The adhesive was coated on the tricot knitted cloth in a coverage rate of about 2 g/m$^2$. Immediately after the adhesive was transferred onto the surface of the cloth which was held in the heated condition, the non-glossy surface of a cellulose acetate membrane filter having an effective pore size of 3.0 μm, a thickness of 140 μm and a porosity of about 80% was placed, in the face-to-face relationship, on the surface of the cloth applied with the dotted pattern of the adhesive. The cloth now being covered with the membrane filter was then passed through a lamination roller pair to bound the cloth to the membrane filter by means of the adhesive dots, whereby an integral laminate was formed. The thus formed laminate was used as the blood cell separating layer.

1-3: Preparation of Finished Multi-layered Analysis Element

The blood cell separating layer prepared by the step 1-2 was laminated on the underlying composite prepared by the step 1-1 while binding the former to the latter through a gravure printing process similar to the process employed in the step 1-1.

Similarly as in the step 1-2, a molten hot-met type adhesive was applied on the free surface of the membrane filter of the blood cell separating layer to form a pattern of dots through a similar gravure printing process. Immediately after the application of the molten adhesive, the free surface of the membrane filter was placed on the surface of the broad woven cloth of the underlying composite of the analysis element, and then passed through a lamination roller pair to form an integrally laminated structure which was used as the multi-layered analysis element in the method of this invention.

The thus finished multi-layered analysis element was cut into 15 mm × 15 mm square pieces. Each piece was contained in the organic polymer slide frame as described, for example, in Unexamined Japanese Patent Publication No. 63452/1982 to prepare a multi-layered analysis slide for the quantitative analysis of AST activity.

EXAMPLE 2

Multi-layered Analysis Element Used for the Quantitative Analysis of ALT (Alanine Adminotransferase) Activity

2-1: Preparation of Underlying Composite of the Analysis Element

Similarly as in Example 1, the same coloring reagent composition used in Example 1 was coated on a PET support.

Then, an adhesive composition as set forth below was coated on the coloring reagent layer, followed by drying, to form a 3 μm thick (in the dried state) adhesive layer having the following coverage of respective ingredients.

| Coverage (per 1 m$^2$) of the Adhesive: | |
|---|---|
| Deionized Gelatin | 4.0 g |
| p-Nonylphenoxypolyglycidol (Containing 10 Glycidol Units on Average) (The pH value of the solution of the adhesive composition was adjusted to pH 7.0 using a dilute aqueous solution of NaOH.) | 160 mg |

The overall surface of the thus formed adhesive layer was wetted uniformly with water, and a PET broad woven cloth (having a thickness of about 150 μm and a volume porosity of 9.8 μl/m$^2$) was placed on the adhesive layer. The broad woven cloth was laminated on the adhesive layer by the application of a light pressure, and then the laminate was dried.

An aqueous solution of an ALT detecting reagent composition having the composition as set forth below was coated over the surface of the laminate uniformly in a ratio of 100 ml/m$^2$ to form a substantially uniform coating which was dried after the coated into solution of the reagent composition was impregnated within the laminate, whereby an underlying composite or laminate for a multi-layered analysis element for the quantitative analysis of ALT activity was prepared.

| Composition of Aqueous Solution of ALT Detecting Reagent: | |
|---|---|
| Tris(hydroxymethyl)aminomethane | 2.2 g |
| Potassium Dihydrogenphosphate (KH$_2$PO$_4$) | 4.5 g |
| α-Ketoglutaric Acid | 4.0 g |
| L-Alanine | 27.5 g |
| Hydroxypropylmethyl Cellulose (Containing 28 to 30% of methoxy groups and 7 to 12% of hydroxypropoxy groups; and having a viscosity at 20° C. of a 2% solution of 50 cps.) | 8.7 g |
| Octylphenoxypolyethoxyethanol (Containing 10 Oxyethylene Units on Average) | 27 g |
| Magnesium Chloride | 2.4 g |
| Water | 880 g |

Prior to coating the aqueous solution of the ALT detecting reagent composition, the pH value thereof was adjusted to pH 7.5 using a dilute aqueous solution of NaOH.

2-2: Preparation of Blood Cell Separating Layer

A blood cell separating layer was prepared by the same process as described in the step 1-2 of Example 1.

2-3: Preparation of Finished Multi-layered Analysis Element

The blood cell separating layer prepared by the step 2-2 was laminated on the underlying composite prepared by the step 2-1, similarly as in the step 1-3 of Example 1. The following procedures were the same as described in the step 1-3 of Example 1, whereby an integrally laminated multi-layered analysis element was prepared. The analysis element was cut into pieces and each piece was contained in the same slide as used in Example 1 to prepare a multi-layered analysis slide for the quantitative analysis of ALT activity.

Each of the analysis element for the quantitative analysis of AST activity (prepared by Example 1) and the analysis element for the quantitative analysis of ALT activity (prepared by Example 2) comprises the underlying composite including the transparent support, the coloring reagent layer and the broad woven cloth laminated one after another in this order; and the blood cell separating layer including the membrane filter and the tricot knitted cloth laminated in this order; the underlying composite layer being laminated with the blood cell separating layer.

The membrane filter and the tricot knitted cloth partially bound to each other by the adhesive dots to form an integral laminate exhibit a co-operative function to separate and remove the blood cells from the whole blood sample spotted on the top surface of the tricot knitted cloth. The tricot knitted cloth serves also as a spreading layer as the whole blood sample is spotted thereon so that the spot of the thus fed whole blood sample is spread radially to wet the cloth substantially uniformly. The broad woven cloth contains the AST detecting reagent composition in the analysis element of Example 1 (the ALT detecting reagent composition in the analysis element of Example 2) which reacts with AST (ALT in the analysis element of Example 2) contained in the plasma passing through the blood cell separating layer to produce pyruvic acid in an amount which is in proportion to the quantity of AST (the quantity of ALT in the analysis element of Example 2) contained in the plasma. The broad woven cloth also serves as a spreading layer to spread the plasma passing therethrough so that a substantially constant volume of plasma is present in a unit area. The coloring reagent layer serves as a layer in which pyruvic acid produced in the broad woven cloth is converted to hydrogen peroxide which is further converted to a dye and accumulated, the amount of the thus formed dye being in proportion to the quantity of AST (in the analysis element of Example 1) or ALT (in the analysis element of Example 2). The dye formed and retained in the coloring reagent layer is optically detected in the subsequent step.

It has been observed empirically that substantially all of blood cells including red blood cells is separated from the whole blood sample spotted on the surface of the tricot knitted cloth of each of the multi-layered analysis elements of Examples 1 and 2 until the liquid sample flows through the membrane filter, so that they do not reach the broad woven cloth. However, since the multi-layered analysis elements prepared by Examples 1 and 2 have no light-shielding layer for preventing detection of the red matters of the red blood cells from the transparent support side, red color due to the presence of red matters of red blood cells separated and trapped by the blood cell separating layer is visually observed through the transparent support.

However, as will be described in detail in the following description of Appraisal Tests, the quantitative analysis of AST or ALT activity of individual whole blood sample was not obstructed by the fact that the red matters of the separated red blood cells are vidually seen from the transparent support side.

Appraisal Test 1

The reflected light is measured from the transparent support side and the change in optical density due to the presence of the coloring matters of the separated blood cells was determined, and the change in optical density due to the formation of the coloring dye which is formed in the presence of the analyte contained in the sample liquid was also determined.

Liquid samples as set forth in Table 1 were prepared. Liquid samples (A) and (C) were sera which were used as controls, and liquid samples (B) and (D) were whole blood samples.

TABLE 1

| Liquid Sample | Hematocrit Value (%) | Content of AST (IU/l) |
|---|---|---|
| (A) | 0 | 0 |
| (B) | 40 | 0 |
| (C) | 0 | 540 |
| (D) | 40 | 540 |

On the tricot knitted cloth of the multi-layered analysis element of Example 1, spotted was 20 μl for each of the liquid samples, and each analysis element was held at 37° C., in a closed incubator. The changes in optical density observed in respective analysis elements were measured using a visual light having a wavelength of 640 nm. The results are shown in FIG. 1. The changing rates in optical density were monitored from the time after the lapse of 3.5 minutes to the time after the lapse of 5 minutes from the time of spotting respective liquid samples. The changing rates per one minute were calucultated. The results are set forth in Table 2.

TABLE 2

| Liquid Sample | Changing Rate in Optical Density (per one minute) |
|---|---|
| (A) | $0.0 \times 10^{-2}$ |
| (B) | $0.0 \times 10^{-2}$ |
| (C) | $3.1 \times 10^{-2}$ |
| (D) | $3.2 \times 10^{-2}$ |

As will be seen from FIG. 1, when the reflected light was detected from the transparent support side, the change in optical density due to the presence of separated blood cells had been saturated within a very short time period (within about 10 seconds), and the optical density of the red dymatterses of the blood cells was not changed after then (see the curves showing the results when liquid samples (A) and (B) were spotted). Coloring of the dye formed in the presence of AST contained in each liquid sample was initiated after the change in optical density due to the presence of separated blood cells had been saturated (see the curves showing the results when liquid samples (C) and (D) were spotted). Accordingly, irrespective of the presence or absence of blood cells, the changing rates in optical density within a unit time are identical when the AST activities in two liquid samples are equivalent.

Similar appraisal tests were conducted while using the multi-layered analysis elements for the quantitative analysis of ALT activity prepared by Example 2. Substantially similar results were obtained.

Appraisal Test 2

Using the multi-layered analysis elements prepared by Examples 1 and 2, activities of AST and ALT in respective whole blood samples were determined to appraise the accuracies of respective quantitative analyses.

Different quantities of AST and ALT were added to a 7% aqueous solution of HSA (human serum albumin) to prepare liquid samples having different AST and ALT activities. Separately, human whole blood was subjected to centrifugal separation to obtain plasma. A portion of the thus obtained plasma was substituted by each of the aforementioned 7% HSA solutions containing different quantities of AST and ALT, and then the separated blood cell fraction was added to each mixture, whereby whole blood samples having a constant hematocrit value of 40% and different AST and ALT activies were prepared.

Figure 2:
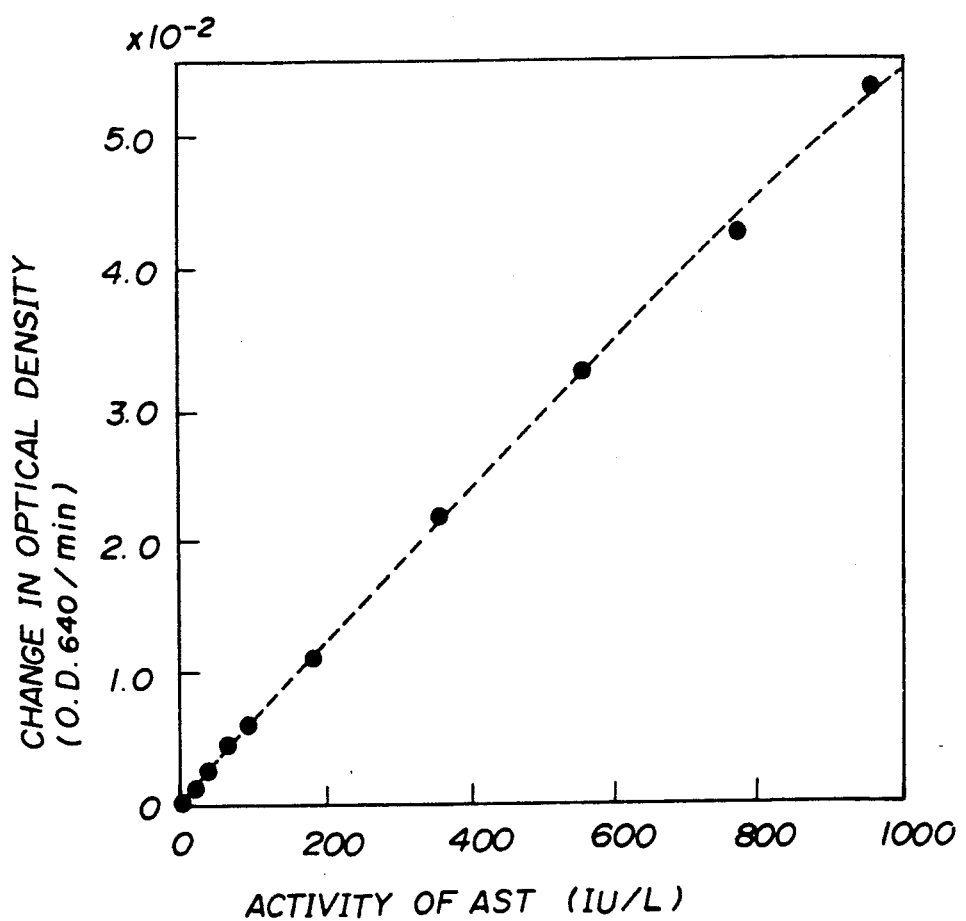
FIG. 2 is a graph showing a calibration curve drawn by plotting the change in optical density of the reflected light per a unit time in terms of the change in AST (aspartate aminotransferase) activity in a whole blood sample.
Figure 3:
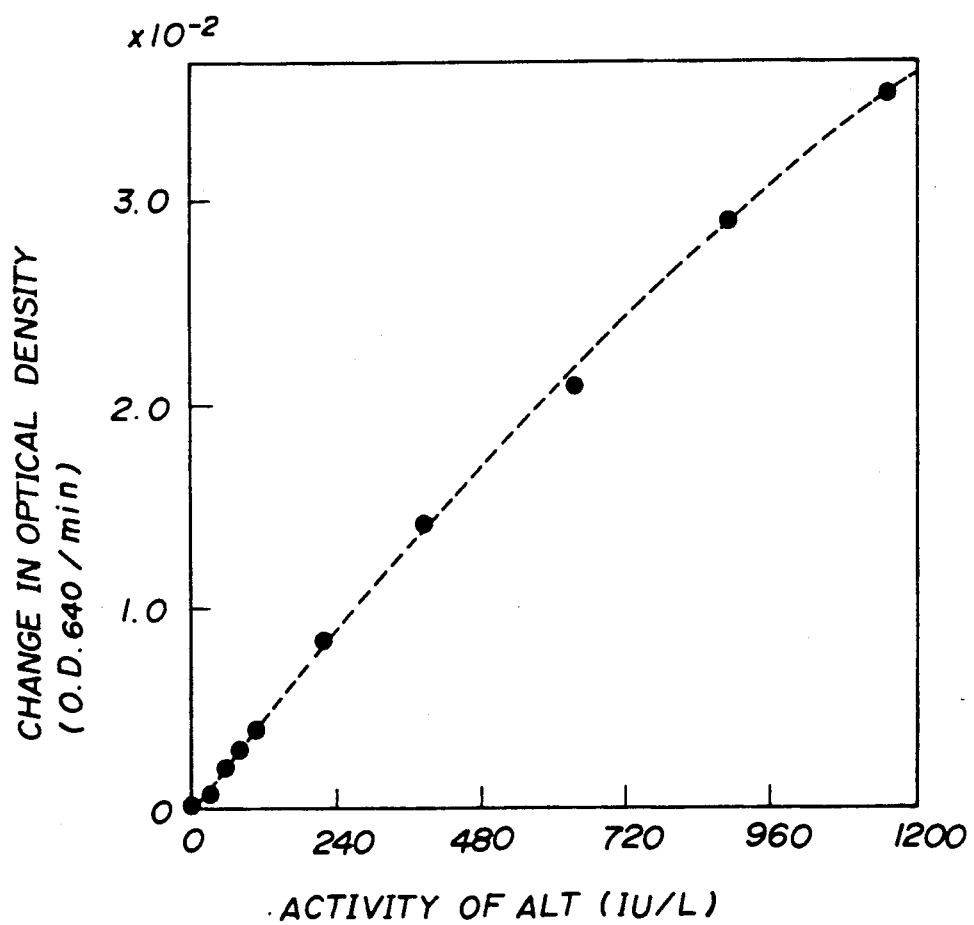
FIG. 3 is a graph showing a calibration curve drawn by plotting the change in optical density of the reflected light per a unit time in terms of the change in ALT (alanine aminotransferase) activity in a whole blood sample.

20 μl for each of the thus prepared whole blood samples was spotted on the tricot knitted cloth of the multi-layered analysis elements prepared by Examples 1 and 2. After holding respective analysis elements at 37° C. in a closed incubator, the changing rates in optical density were monitored from 3.5 minutes to 5 minutes after the time of spotting the samples. The results are shown in FIGS. 2 and 3 and Table 3.

The AST and ALT activities set forth in Table 3 were determined by analyzing the plasma, which was obtained by subjecting each of the whole blood sample to centrifugal operation, through a wet process.

TABLE 3

| Sample No. | AST Activity (IU/l) | ALT Activity (IU/l) | Changing Rate in Optical Density (per one minute) | |
|---|---|---|---|---|
| | | | Example 1 × $10^{-2}$ | Example 2 × $10^{-2}$ |
| (a) | 1 | 1147 | 0.3 | 3.53 |
| (b) | 20 | 886 | 0.14 | 2.91 |
| (c) | 37 | 632 | 0.26 | 2.11 |
| (d) | 67 | 383 | 0.45 | 1.43 |
| (e) | 93 | 213 | 0.59 | 0.84 |
| (f) | 181 | 105 | 1.11 | 0.40 |
| (g) | 351 | 79 | 2.15 | 0.30 |
| (h) | 550 | 54 | 3.20 | 0.21 |
| (i) | 771 | 28 | 4.21 | 0.08 |
| (j) | 954 | 1 | 5.27 | 0.03 |

As will be seen by referring to the data set forth in Table 3 and the graphs shown in FIGS. 2 and 3, when the change in optical density of the reflected light was measured from the transparent support side (the side exposed to the light used for the measuring operation) after the change in optical density due to the red matters in the separated blood cells have been saturated, the changing rate in optical density of the reflected light due to coloring reaction of AST is propotional to the activity of AST when the samples are spotted on the multi-layered analysis element of Example 1 for the quantitative analysis of AST, and also proportional to the activity of ALT when the samples are spotted on the multi-layered analysis element of Example 2 for the quantitative analysis of ALT.

Appraisal Test 3

The following tests were conducted to appraise the influence by the hematocrit value on the accuracy of the quantitative analysis of activities of AST and ALT when the multi-layered analysis elements of Examples 1 and 2 were used and whole blood samples were spotted thereon. The general procedures are similar to those as described in Appraisal Test 1.

Different quantities of AST and ALT were added to a 7% aqueous solution of HSA to prepare three liquid samples having different AST and ALT activities and dissolved in the 7% HSA solution. Separately, human whole blood was subjected to centrifugal separation to obtain plasma. A portion of the thus obtained plasma was substituted by each of the aforementioned 7% HSA solutions containing different quantities of AST and ALT, whereby whole blood samples having different AST and ALT activities were prepared. Then, after subjecting respective whole blood samples to centrifugal separation, a certain volume of separated plasma wa removed from or added to respective whole blood samples, whereby whole blood samples having different AST and ALT activities and each having a hematocrit value of 25%, 40% and 55% were prepared.

20 μl for each of the thus prepared whole blood samples was spotted on the tricot knitted cloth of the multi-layered analysis elements prepared by Examples 1 and 2. After holding respective analysis elements at 37° C. in a closed incubator, the changing rates in optical density were monitored from 3.5 minutes to 5 minutes after the time of spotting the samples.

The changing rates in optical density were converted into the AST and ALT activities of respective samples while referring to the interrelation between the changing rate in optical density and the AST and ALT activities as shown in FIGS. 2 and 3. The results are shown in Table 4. Meanwhile, the results of the samples each having a hematocrit value of 0% are given in Table 4 to show the results when plasma samples containing no blood cells are analyzed.

TABLE 4

| Sample No. | Hematocrit Value (%) | Example 1 AST Activity (IU/l) | Example 2 ALT Activity (IU/l) |
|---|---|---|---|
| I | 0 | 72 | 462 |
| | 25 | 76 | 464 |
| | 40 | 78 | 458 |
| | 55 | 76 | 455 |
| II | 0 | 163 | 172 |
| | 25 | 170 | 174 |
| | 40 | 170 | 168 |
| | 55 | 167 | 166 |
| III | 0 | 428 | 55 |
| | 25 | 438 | 57 |
| | 40 | 440 | 53 |
| | 55 | 436 | 52 |

As will be seen from the results set forth in Table 4, the changing rates in optical density of the reflected light (the activities of analytes corresponding to the changing rates are shown in Table 4) were not significantly affected by the change in hematocrit value, both in the analysis elements prepared by Examples 1 and 2. In other words, the influence on the results of measurement due to the presence of red matters (mainly the presence of hemoglobin) in the blood cells in the whole blood samples could be excluded to the least extent.

Meantime, it has been known that relatively large amounts of AST and ALT are present in the red blood cells which are main components of blood. The activity of AST contained in red blood cells amount to about 80 times as high as the activity of AST contained in the plasma, and the activity of ALT contained in red blood cells amount to about 15 times as high as the activity of ALT contained in the plasma. With the aforementioned knowledge in view, the result set forth in Table 4 reveals that substantially no hemolysis of red blood cells occurs in the multi-layered analysis elements of Examples 1 and 2.

What is claimed is:

1. In the method of quantitatively analyzing an analyte in a whole blood sample by using a multi-layered analysis element including at least a coloring reagent layer in which said analyte reacts with a reagent composition to exhibit an optically detectable color change or color generation and a blood cell separating layer for separating the blood cells in the whole blood to feed blood plasma to said reagent layer, an improved method comprising the steps of:
   (1) spotting a whole blood sample onto said blood cell separating layer;
   (2) allowing said multi-layered analysis element to stand until the optical density of the reflected light due to the coloring matters contained in the blood cells detected from the coloring reagent layer side reaches a substantially constant level;
   (3) measuring the rate of change in optical density within a unit time in said coloring reagent layer from the coloring reagent layer side; and
   (4) colorimetrically determining the quantity of said analyte depending on the rate of change in optical density measured by the preceding step (3).

2. The method according to claim 1, wherein said blood cells have been separated from said whole blood in said blood cell separating layer before said change in optical density caused by the reaction of said analyte with said reagent composition within said reagent layer is detected.

3. The method according to claim 1, wherein said coloring matters contained in said blood cells and separated in said blood cell separating layer are optically detectable from the coloring reagent layer side.

4. The method according to claim 1, wherein the detected optical density of said coloring matters contained in said blood cells is a substantially constant value after the completion of separation of said blood cells by said blood cell separating layer.

5. The method according to claim 1, wherein said blood cell separating layer of said multi-layered analysis element comprises an upper layer composed of a fibrous porous material and a lower layer composed of a non-fibrous porous material.

6. The method according to claim 5, wherein said lower layer is laminated with said upper layer by partial bonding.

7. The method according to claim 5 or 6, wherein said lower layer is a membrane filter composed of a blush polymer and having a glossy face disposed at the side farthest from said upper layer.

8. The method according to claim 1, wherein said coloring reagent layer is integrally bound to said blood cell separating layer by an adhesive distributed to allow uniform passage of a liquid sample from said blood cell separating layer to said coloring reagent layer.

9. The method according to claim 1, wherein said multi-layered analysis element further comprises a water-impermeable and light-permeable support on which said coloring reagent layer and said blood cell separating layer are laminated in this order so that the optical density of said coloring reagent layer and the optical density of said blood cell separating layer are measured from said coloring reagent layer through said support.

10. In the method of quantitatively analyzing an analyte in a whole blood sample by using a multi-layered analysis element including at least a coloring reagent layer in which said analyte reacts with a reagent composition to exhibit an optically detectable color change or color generation and a blood cell separating layer for separating the blood cells in the whole blood to feed blood plasma to said reagent layer, an improved method comprising the steps of:
   (1) spotting a whole blood sample onto said blood cell separating layer;
   (2) allowing said multi-layered analysis element to stand until a measurement of optical density of the reflected light due to the coloring matters contained in the blood cells measured from the coloring reagent layer side reaches a substantially constant level;
   (3) measuring the total optical density of the reflected light from the coloring reagent layer side, said total optical density being the sum of the optical density of the reflected light due to the color change or color generation of said analyte and the optical density of the reflected light due to the coloring matters contained in the blood cells;
   (4) determining the difference in optical density between said total optical density measured in said step (3) and the optical density measured in said step (2); and
   (5) colorimetrically determining the quantity of said analyte depending on the difference in optical density determined by the preceding step (4).

11. The method according to claim 10, wherein said blood cells have been separated from said whole blood in said blood cell separating layer before said change in optical density caused by the reaction of said analyte with said reagent composition within said reagent layer is measured.

12. The method according to claim 10, wherein said coloring matters contained in said blood cells and separated in said blood cell separating layer are optically measured from the coloring reagent layer side.

13. The method according to claim 10, wherein the measured optical density of said coloring matters contained in said blood cells is a substantially constant value after the completion of separation of said blood cells within said blood cell separating layer.

14. The method according to claim 10, wherein said blood cell separating layer of said multi-layered analysis element comprises an upper layer composed of a fibrous porous material and a lower layer composed of a non-fibrous porous material.

15. The method according to claim 14, wherein said lower layer is laminated with said upper layer by partial bonding.

16. The method according to claim 14 or 15, wherein said lower layer is a membrane filter composed of a blush polymer and having a glossy face disposed at the side farthest from said upper layer.

17. The method according to claim 10, wherein said coloring reagent layer is integrally bound to said blood cell separating layer by an adhesive distributed to allow uniform passage of a liquid sample from said blood cell separating layer to said coloring reagent layer.

18. The method according to claim 10, wherein said multi-layered analysis element further comprises a water-impermeable and light-permeable support on which said coloring reagent layer and said blood cell separating layer are laminated in this order so that the optical density of said coloring reagent layer and the optical density of said blood cell separating layer are measured from said coloring reagent layer through said support.

* * * * *